United States Patent [19]

Sano et al.

[11] 3,997,644

[45] Dec. 14, 1976

[54] METHOD FOR MANUFACTURING NOVEL CATION EXCHANGERS

[75] Inventors: Takezo Sano, Takatsuki; Akira Kobayashi, Ibaragi; Ichiki Murase, Tokyo, all of Japan

[73] Assignee: Sumitomo Chemical Company, Limited, Osaka, Japan

[22] Filed: Sept. 16, 1974

[21] Appl. No.: 506,023

[30] Foreign Application Priority Data

Sept. 19, 1973 Japan ............................. 48-106223

[52] U.S. Cl. .......................... 264/122; 162/157 R; 260/2.1 R; 260/2.2 R; 264/126; 264/234
[51] Int. Cl.² ........................................... C08J 1/34
[58] Field of Search ..................... 260/2.2 R, 2.1 R; 264/126, 234, 122, 109; 162/146, 157 R

[56] References Cited
UNITED STATES PATENTS

| 3,092,438 | 6/1963 | Kruger, Jr. | 264/126 |
|---|---|---|---|
| 3,248,339 | 4/1966 | Spes et al. | 264/122 |
| 3,271,292 | 9/1966 | Kollsman | 264/109 |
| 3,452,128 | 6/1969 | Rains | 264/126 |
| 3,453,354 | 7/1969 | Tejeda et al. | 264/126 |
| 3,501,369 | 3/1970 | Drelich et al. | 264/126 |
| 3,645,922 | 2/1972 | Weiss et al. | 260/2.1 R |
| 3,787,256 | 1/1974 | Nowotny | 162/146 |
| 3,816,357 | 6/1974 | Church | 260/2.2 R |

*Primary Examiner*—Jeffery R. Thurlow
*Attorney, Agent, or Firm*—Stevens, Davis, Miller & Mosher

[57] ABSTRACT

A cation exchanger in paper-like or felt-like form is obtained by making a fibrous sheet from a blend of polyethylene fibers into which sulfonic groups have been introduced with 0.1 to 50% by weight of thermoplastic resin fibers and heating the sheet at the softening temperature of said thermoplastic resin or higher temperatures. This cation exchanger is useful in softening or desalination of raw water, separation and recovery of various metals, and adsorption of basic dyestuffs and cationic dyestuffs.

3 Claims, No Drawings

METHOD FOR MANUFACTURING NOVEL CATION EXCHANGERS

This invention relates to a novel cation exchanger and, more particularly, to a paper-like or felt-like cation exchanger made from polyethylene fibers introduced with sulfonic groups as major component.

It is well known that ion exchangers have become widely used not only in water purification and raw-water treatment, but also in purification or organic substances, as catalysts for various reactions, and as adsorbents for gases.

Depending upon the intended use, ion exchangers are used in various forms, beside widely used spheric or amorphous granules of 20 to 40 mesh. Also depending upon the intended use, ion exchangers having various ionizable groups are used; for example, in the case of cation exchangers, those having such functional groups as sulfonic acid group, phosphoric acid group, carboxyl group, and phenolic hydroxyl group are used. Among cation exchangers, most widely used are those obtained by sulfonation from a base material of a styrenedivinylbenzene copolymer. Such exchangers, however, are not satisfactory in view of mechanical strengths and alkali resistance.

An object of this invention is to provide an ion exchanger in paper-like form and felt-like form made from polyethylene fibers introduced with sulfonic groups as major component.

Other objects and advantages of this invention will become apparent from the following description.

The present inventors had formerly found that a useful fibrous cation exchanger may be obtained by sulfonation of polyethylene fibers and as the result of continued studies on its improvement have now succeeded in producing a cation exchanger having a wider application field, by the method disclosed below.

According to this invention, there is obtained a paper-like or a felt-like cation exchanger which is low in cost, considerably high in ion-exchange capacity and does not swell, dissolve, or deteriorate when used not only in aqueous solutions, but also in organic solvents.

Since the present cation exchanger is obtained by sulfonation of polyethylene in the form of fiber, it is possible to impart higher cation exchanging ability to the portion near the fiber surface. The outstanding feature of such a cation exchanger is the rapidity of diffusion and exchange of ions which take place in the vicinity of the fiber surface, being quite different from the case of crosslinked ion exchangers such as a styrene-divinylbenzene type and other conventional ion exchangers where ion exchange takes place within narrow pores.

Further, because of its paper-like or felt-like form, the present exchanger is advantageous in mounting on and dismounting from the apparatus when it is used.

The polyethylene fiber to be subjected to sulfonation can be manufactured by known methods such as melt spinning, flash spinning, cutting and splitting a stretched tape into fibers, and polymerization under shearing stress to yield a fibrous polymer.

Although a polyethylene fiber in filament form can, of course, be used, particularly preferred for the purpose of introduction of sulfonic acid group are those obtained by a so-called flash spinning method in which a polyethylene solution is ejected under applied pressure through a nozzle. The fibrous polyethylene obtained by the flash spinning is of low cost and had a large surface area because of its three-dimensional network structure of fine fibers having a diameter of 1 to 5 $\mu$.

These fibrous polyethylenes are beaten to form a pulp so that they may be made into a fibrous sheet.

Introduction of sulfonic groups can be effected by conducting the reaction between polyethylene and, for example, a halosulfonic acid such as chlorosulfonic acid or sulfur trioxide by use or without use of a diluent solvent for the reaction.

The sulfonation degree of the sulfonated polyethylene fiber thus obtained can be estimated from the sulfur content as measured by elementary analysis. A suitable sulfur content for the present purpose is 2 to 20%, preferably 5 to 18%, by weight. The sulfonation degree can also be estimated from determination of the ion-exchange capacity. A suitable ion exchange capacity for the present purpose is 0.2 to 10 milliequivalent per 1 g of dry H-ion loaded exchanger. If the ion-exchange capacity is below the lower limit, the exchanger is undesirably hydrophobic, while if it exceeds the upper limit, the fiber becomes brittle.

The sulfonated polyethylene fiber in pulp form is blended with a suitable amount, for example, 0.1 to 50%, preferably 5 to 30%, by weight, of a thermoplastic resin fiber such as, for example, polyethylene fiber, polypropylene fiber, or polystyrene fiber in pulp form on th basis of the total fibers and formed into sheet by use of water, and heated at the softening temperature of said thermoplastic resin or at higher temperatures to obtain the intended novel cation exchanger in the form of paper or felt.

The thickness of the exchanger is suitably selected depending on the volume of sulfonated polyethylene fibers and that of thermoplastic resin fibers to be used and on the area of sheet to be formed. It is generally 0.01 to 10 mm, preferably 0.1 to 5 mm. The bulk density of the exchanger, which is associated with the freeness of the exchanger, can be adjusted by controlling the way of pressing in sheet making as well as the way of subsequent heat treatment.

The cation exchanger obtained according to this invention ranges from hard paper-like material to soft felt-like material. It retains sufficient strength without losing the shape when used as a filter in contact with water or organic solvents. It is simple in handling, permits rapid diffusion and exchange of ions owing to the distribution of active centers over a large surface area, and hence, makes possible to design a simple and small ion exchange device, thus offering a great advantage to the industry.

By virtue of the aforesaid characteristic advantages, the cation exchanger thus obtained according to this invention is useful not only in desalination and softening of raw water, but also in a variety of fields such as separation and recovery of various metals and adsorption of basic and cationic dyestuffs.

The invention is illustrated below in detail with reference to Examples, but the invention is not limited to the examples.

EXAMPLE 1

A blend was prepared in methanol from 1.35 g of high-density polyethylene staple fibers having three-dimensional network structure, which had been sulfonated with chlorosulfonic acid, and 0.15 g of high-density polyethylene staple fibers having three-dimensional network structure, which had not been sulfonated. A fibrous sheet was made from the blend in methanol, dried, and then heat treated in an oven at 135° C. for 3 minutes. The resulting black felt-like material, 2 to 3 mm in thickness, was mounted on a filter holder and a 5-ppm aqueous solution of Sumiacryl Brilliant N-4G (a cationic dyestuff produced by Sumitomo Chemical Co.) was passed through the felt-like material at a space velocity of 5,000/hour. The effluent obtained was perfectly colorless. The experiment was repeated under the same conditions as mentioned above, except that 1.5 g of a granular cation exchange resin filled in a column was used. No decoloring of the effluent was observed.

EXAMPLE 2

An ion exchanger in felt form prepared in a manner similar to that in Example 1 was mounted on a filter holder and a 100-ppm aqueous solution of magnesium chloride was passed through the said exchanger to obtain an effluent containing 5 ppm or less of magnesium chloride. The experiment was repeated under the same conditions, except that 1.5 of a granular cation exchange resin filled in a column was used. Concentration of the magnesium chloride in the effluent was 98 ppm.

EXAMPLE 3

A blend was prepared in water from 1.2 g of high-density polyethylene staple fibers having three-dimensional network structure, which had been sulfonated with fuming sulfuric acid, and 0.3 g of high-density polyethylene staple fibers having three-dimensional network structure, which had not been sulfonated. A fibrous sheet was made from the blend in water, dried, and then heat treated in an oven at 135° C for 5 minutes. The resulting black felt-like material, 2 to 3 mm in thickness, was mounted on a filter holder and nitrogen containin 70 ppm of ammonia gas was passed through the felt-like material at a space velocity of 200,000/hour. The concentration of ammonia gas in the exhausted nitrogen was 2 ppm or less.

EXAMPLE 4

A blend was prepared in water from 1.35 g of high-density polyethylene staple fibers having three-dimensional network structure, which had been sulfonated with sulfur trioxide, and 0.15 g of polypropylene staple fibers. A fibrous sheet was made from the blend in water, dried and then heat treated in an oven at 165° C for 5 minutes. The resulting black felt-like material, 2 to 3 mm in thickness, was mounted on a filter holder and 2 ppm aqueous solution of mercuric chloride was passed through the felt-like material at a space velocity of 100/hour to obtain an effluent containing 0.05 ppm or less of mercuric ions.

EXAMPLE 5

A blend was prepared in water from 1.35 g of high-density polyethylene staple fibers having three-dimensional network structure, which had been sulfonated with sulfur trioxide, with 0.15 g of polystyrene staple fibers. A fibrous sheet was made from the blend in water, dried and then heat treated in an oven at 110° C for 3 minutes. The resulting black felt-like material, 2 to 3 mm in thickness, was mounted on a filter holder and an aqueous solution of cadmium acetate containing 2 ppm of cadmium ions was passed through the felt-like material at a space velocity of 100/hour to obtain an effluent containing 0.02 ppm or less of cadmium ions.

EXAMPLE 6

A cation exchanger prepared by the same manner as in Example 1 was cut to obtain a round sheet of 47 mm in diameter (3 mm in thickness) and placed in a 200 ml of beaker. 10 ml of aqueous solution containing each 0.2 ppm of mercuric chloride, cadmium acetate and lead acetate in terms of $Hg^{++}$, $Cd^{++}$ and $Pb^{++}$, respectively, was charged nto the above-mentioned beaker to contact with the cation exchanger and the solution was allowed to stand for 5 minutes with occasional shaking. Thereafter, the cation exchanger was placed on Nutsche funnel, washed with water and then dried in air. The surface of the thus obtained cation exchanger was applied with collodion and dried. The cation exchanger was subjected to analysis with a fluorescent X-ray analyzer (manufactured by Rigaku Denki Co.). By comparing the results obtained with the calibration curve which had been previously obtained, it was recognized that the concentration of $Hg^{++}$, $Cd^{++}$, and $Pb^{++}$ in the sample solution used was 0.19, 0.20, and 0.18 ppm, respectively. The time used for said analysis was about 15 minutes.

What is claimed is:

1. A method for manufacturing a cation exchanger, which comprises blending polyethylene fibers having sulfur content of 2 to 20% by weight, into which sulfonic groups have been introduced, with thermoplastic resin fibers which are at least one member selected from the group consisting of polyethylene fibers, polypropylene fibers and polystyrene fibers in pulp form, wherein 0.1 to 50% by weight of the thermoplastic resin fibers is blended on the basis of total fibers, forming the resulting blend into a fibrous sheet in water or methanol, and treating the sheet at a temperature which is at least the softening point of said thermoplastic resin fibers.

2. A method according to claim 1, wherein the form of the exchanger is paper-like.

3. A method according to claim 1, wherein the form of the exchanger is felt-like.

* * * * *